United States Patent [19]
McClelland et al.

[11] Patent Number: 6,016,701
[45] Date of Patent: *Jan. 25, 2000

[54] ULTRASONIC INSPECTION SYSTEM

[75] Inventors: Richard G. McClelland, Richland; Lawrence R. Fox; Edward J. Ruzauskas, both of Kennewick; Douglas A. Adkisson, Richland, all of Wash.

[73] Assignee: Siemens Power Corporation, Richland, Wash.

[ * ] Notice: This patent is subject to a terminal disclaimer.

[21] Appl. No.: 08/987,490

[22] Filed: Dec. 9, 1997

[51] Int. Cl.⁷ .................................................. G01N 29/10
[52] U.S. Cl. ............................................................ 73/620
[58] Field of Search .............................. 73/620, 627, 628, 73/635, 636, 641, 625; 376/249

[56] References Cited

U.S. PATENT DOCUMENTS

| | | | |
|---|---|---|---|
| 3,937,068 | 2/1976 | Jor | 73/636 |
| 4,826,650 | 5/1989 | Richardson et al. | 73/620 |
| 5,692,024 | 11/1997 | McClelland et al. | 73/620 |

*Primary Examiner*—John E. Chapman
*Attorney, Agent, or Firm*—Ira Lee Zebrak

[57] ABSTRACT

An ultrasonic inspection system for ultrasonic inspection of the guide structure of a reactor pressure vessel having two shear wave transducers, one positioned to face in a first direction about 30° from normal to a top edge of the grid members of the top guide structure and a second one positioned to face in a second direction about 30° from normal to a top edge of the grid members of the top guide.

2 Claims, 11 Drawing Sheets

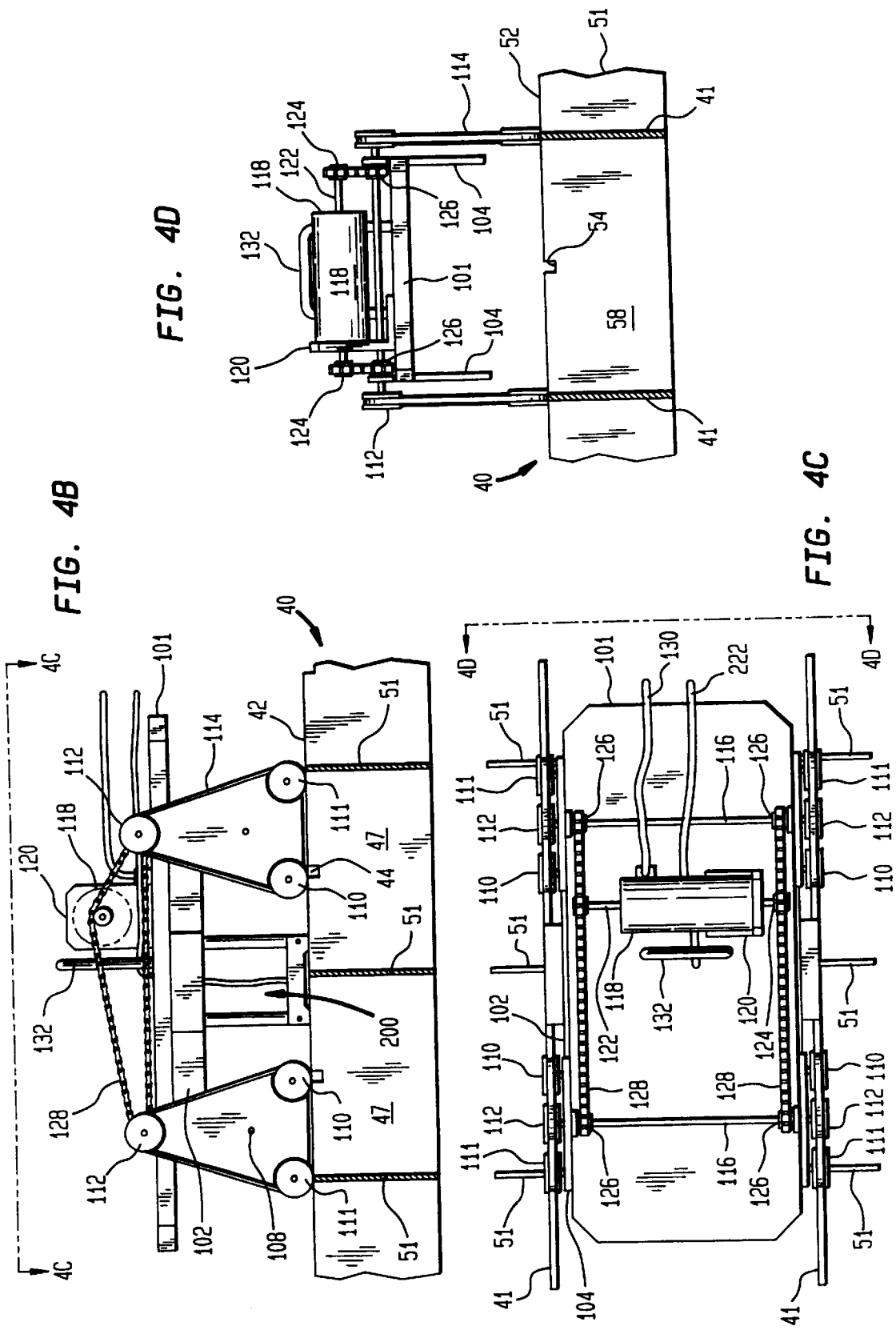

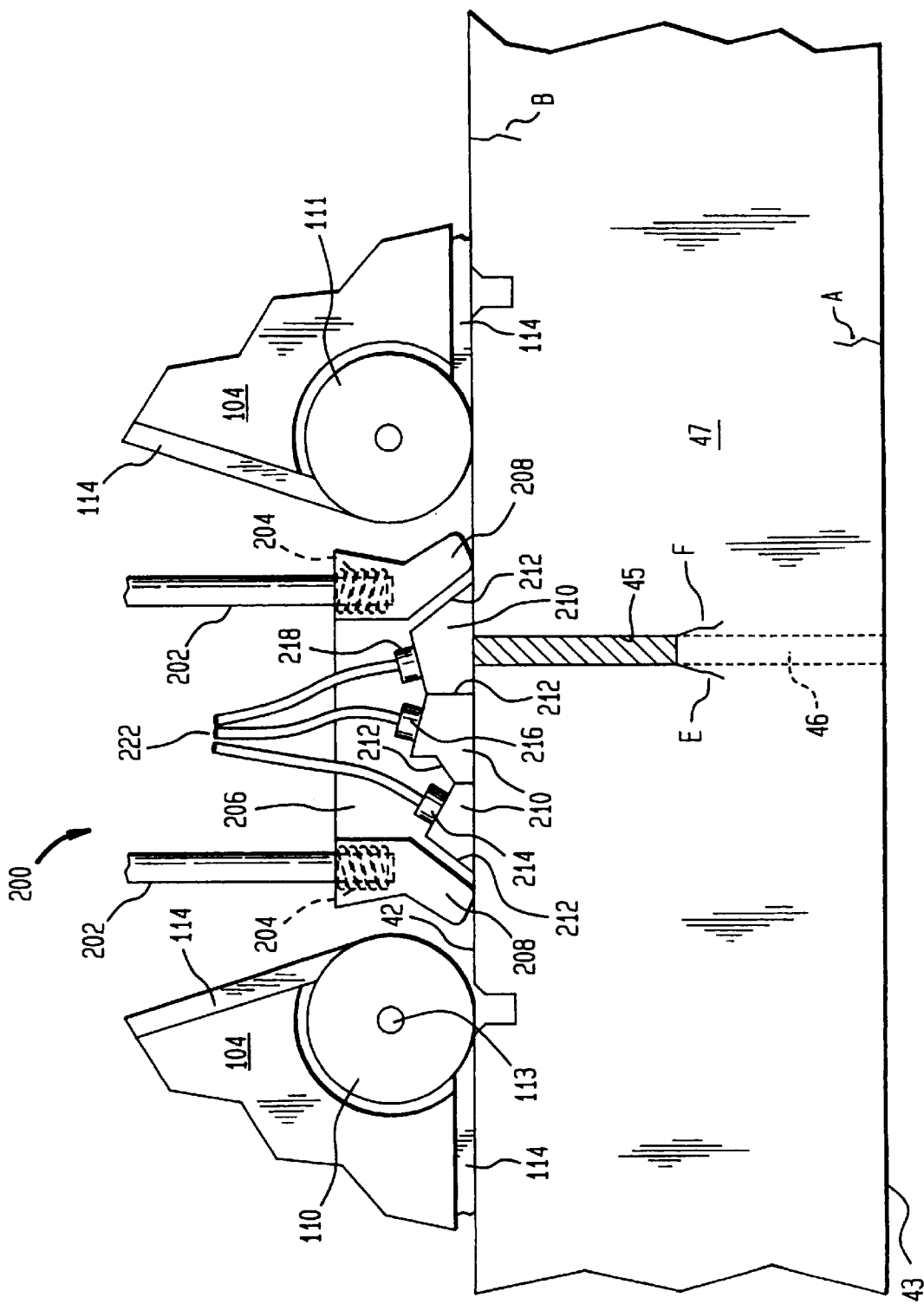

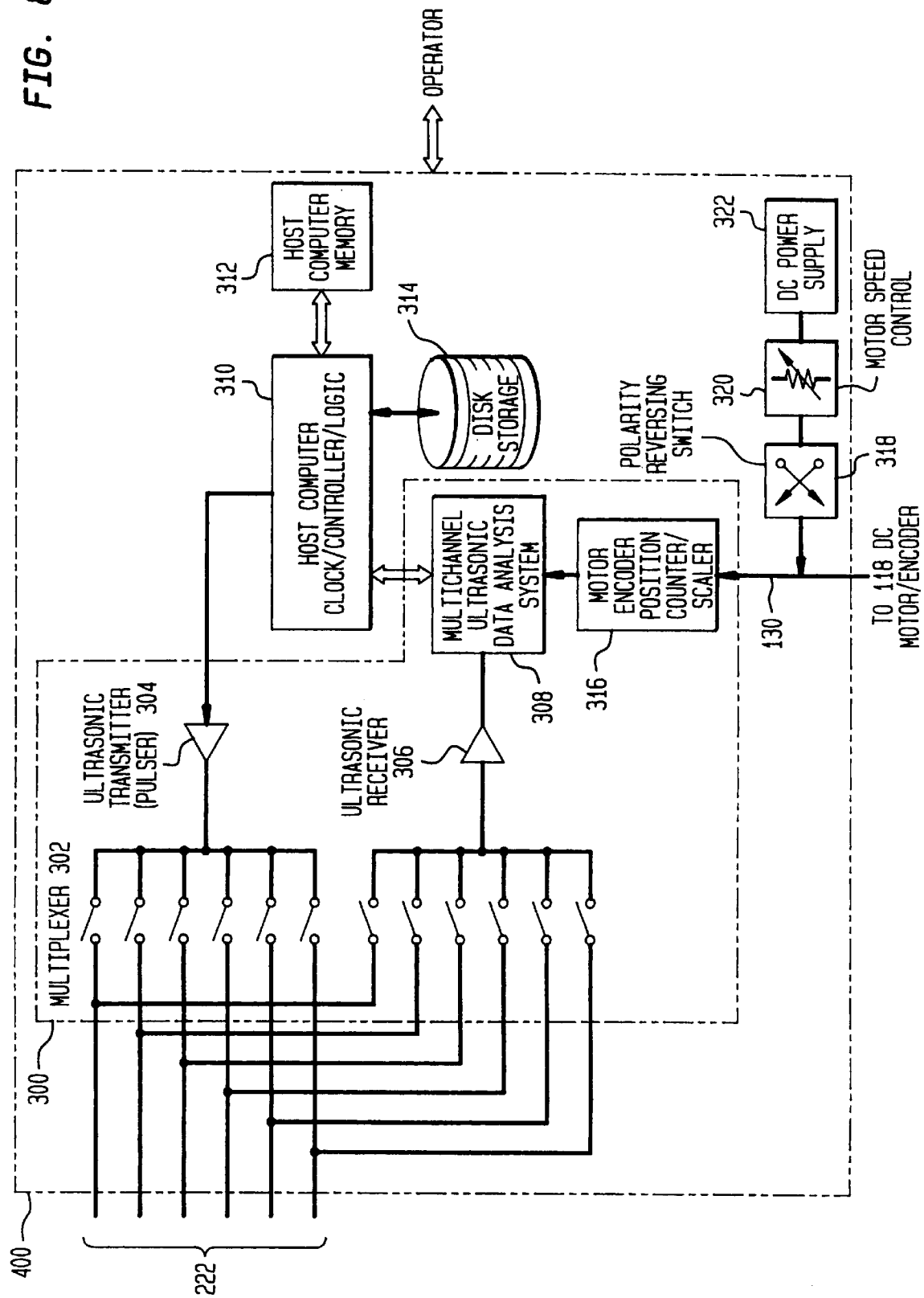

ULTRASONIC INSPECTION SYSTEM

FIELD OF THE INVENTION

The present invention relates generally to an ultrasonic inspection apparatus and method for examining and detecting cracks in the top guide structure of boiling water reactor pressure vessels, and more particularly, for volumetrically inspecting the top guide structure of a fully-loaded boiling water reactor core.

BACKGROUND OF THE INVENTION

Nuclear reactors need to be periodically maintained and inspected as well as refueled. During refueling operations, refueling of the core and related fuel operations are performed, as well as on-site inspection and maintenance within the reactor vessel of reactor pressure vessel internals which are otherwise inaccessible during reactor operations.

Several boiling water reactors have experienced cracks or defects resulting from radiation assisted stress corrosion cracking and intergranular stress corrosion cracking in the reactor pressure vessel top guide structure which serves to align and maintain the upper portion of the fuel assemblies in proper position.

In the past, remote visual examination has been used to locate and characterize these defects. Due to both the construction of the top guide structure which is comprised of two sets of straight parallel grid members which are interconnected to form a lattice of rectangular shaped openings, and the position of the upper ends of the fuel assemblies within these openings, many areas of the top grid structure cannot be accessed or cannot be adequately inspected by visual examination. Areas of the grid members which intersect one another or are underneath one or the other cannot be inspected by visual examination. When cracking or defects occur, the grid members obscure from view the resultant cracks or defects. Areas of the top guide structure which are inaccessible to visual examination have frequently gone uninspected. Even in those limited areas of the top guide structure which can be seen, visual inspection is inherently inadequate to identify defects which are too small to be visually detected. Furthermore, visual examination of even those portions of the top guide structure which can be seen, cannot adequately characterize the depth of a defect which is of equal if not greater importance than identifying the existence of a defect. Even for those areas which can be visually inspected and defects identified, visual inspection cannot be relied upon to provide accurate defect sizing.

Recording the results of visual examination of the plethora of grid members of the top guide structure can be, and frequently is, subject to error due to the difficulty of correlating the presence and location of a defect in a particular grid member to a frame of reference of all the grid members of the top guide structure. Since inspection of the top guide structure has to be performed remotely and underwater, errors due to parallax can significantly impair the accuracy of the results.

In order to inspect even those portions of the top guide structure which can be visually inspected (other than the top edge of the grid members), the nuclear fuel assemblies which are positioned in the openings in the top guide structure have had to be removed. Accordingly, all or at least some of the nuclear fuel assemblies have had to be at least lifted from the reactor core and probably removed from the reactor pressure vessel in order to permit the performance of even a limited visual inspection. In addition, in order to perform visual inspections, the fuel handling machine needs to be continuously available rendering it effectively unavailable for refueling operations or for other purposes even after the fuel assemblies have been removed from the reactor vessel. The need to first remove some or all of the nuclear fuel assemblies from the reactor core or reactor pressure vessel to perform an inspection of the top guide structure involves several days of critical inspection time which can be very costly because of increased refueling outage time.

It would therefore be an advantage and is an object of the present invention to provide a ultrasonic inspection system and method and for inspecting the top guide structure in boiling water reactor pressure vessels for cracks or defects which avoids or overcomes the above-stated disadvantages and which does so remotely, more effectively and accurately, and without the necessity to remove any of the fuel assemblies from the reactor core.

SUMMARY OF THE INVENTION

In accordance with the present invention, an ultrasonic inspection system is provided for ultrasonically inspecting a top guide structure of a reactor pressure vessel of a nuclear reactor, the top guide structure comprised of two sets of parallel grid members which are interconnected to form a lattice of rectangular shaped openings, said inspection system comprising two shear wave transducers and a creeping wave transducer, a first one of the two shear wave transducers positioned to face in a first direction about 30° from normal to a top edge of the two sets of parallel grid members of the top guide structure and a second one of the two shear wave transducers positioned to face in a second direction about 30° from normal to the top edge of the two sets of parallel grid members of the top guide structure.

BRIEF DESCRIPTION OF THE DRAWINGS

FIG. 4B is a side view of the reactor pressure vessel top guide structure inspection apparatus and transport system which positions the Ultrasonic Inspection System on the top guide structure in FIG. 3 taken along line 4B—4B;

FIG. 4C is a top view of the reactor pressure vessel top guide structure inspection apparatus and transport system shown in FIG. 4B taken along line 4C—4C;

FIG. 4D is an end view of the reactor pressure vessel top guide structure inspection apparatus and transport system shown in FIG. 4C taken along line 4D—4D;

FIG. 5 is an enlarged side view of the Ultrasonic Inspection Apparatus of the reactor pressure vessel top guide structure inspection apparatus and transport system shown in FIGS. 3–4 for the inspection of the top guide structure;

FIG. 8 is a block diagram of the data acquisition and control circuits.

DETAILED DESCRIPTION OF THE INVENTION

Figure 1:
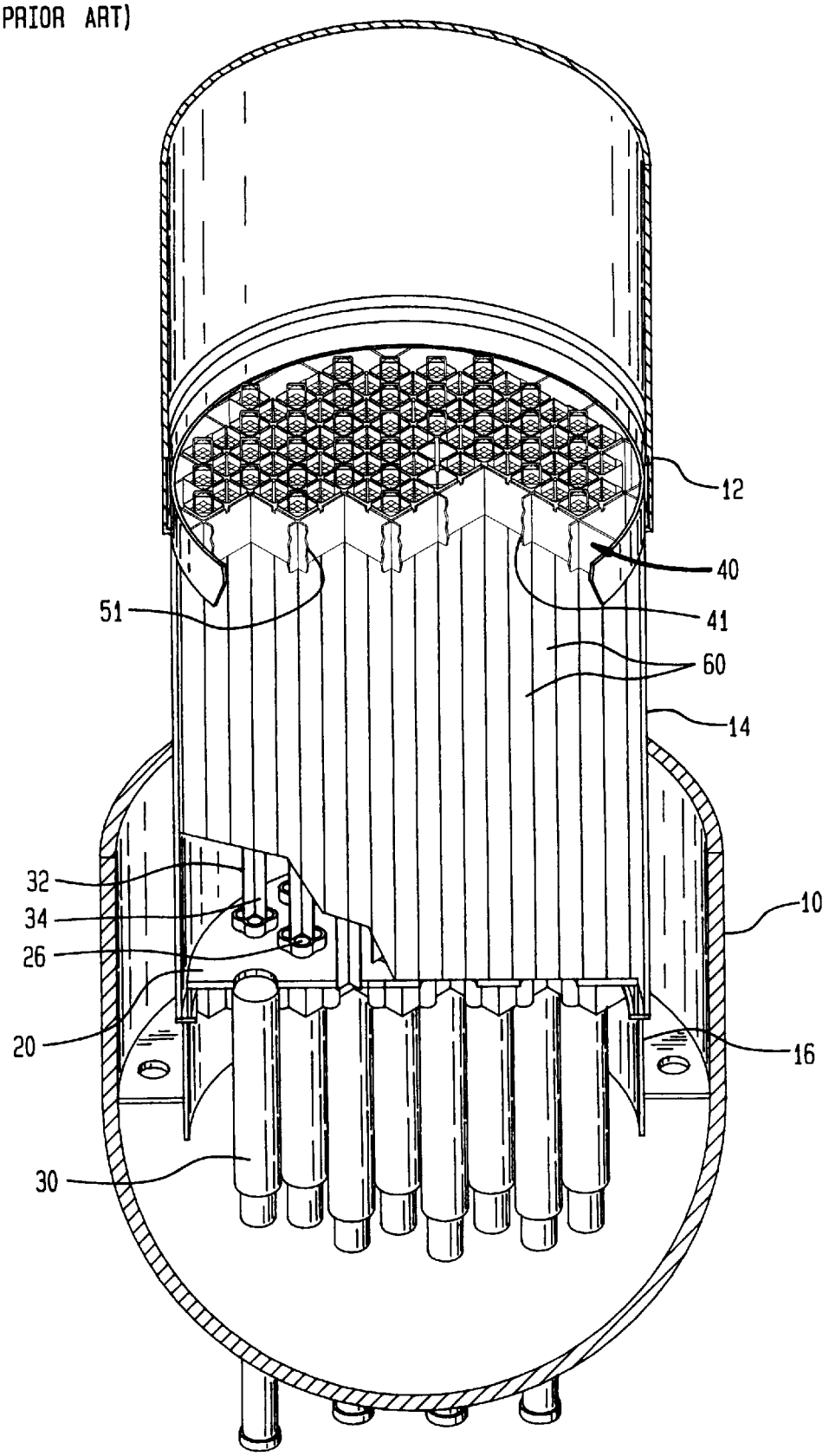
FIG. 1 is a schematic illustration of the inside of a reactor pressure vessel for a boiling water reactor (BWR) during refueling operations showing the nuclear fuel assemblies positioned in the reactor core between the core support plate and the top guide structure.
Figure 2:
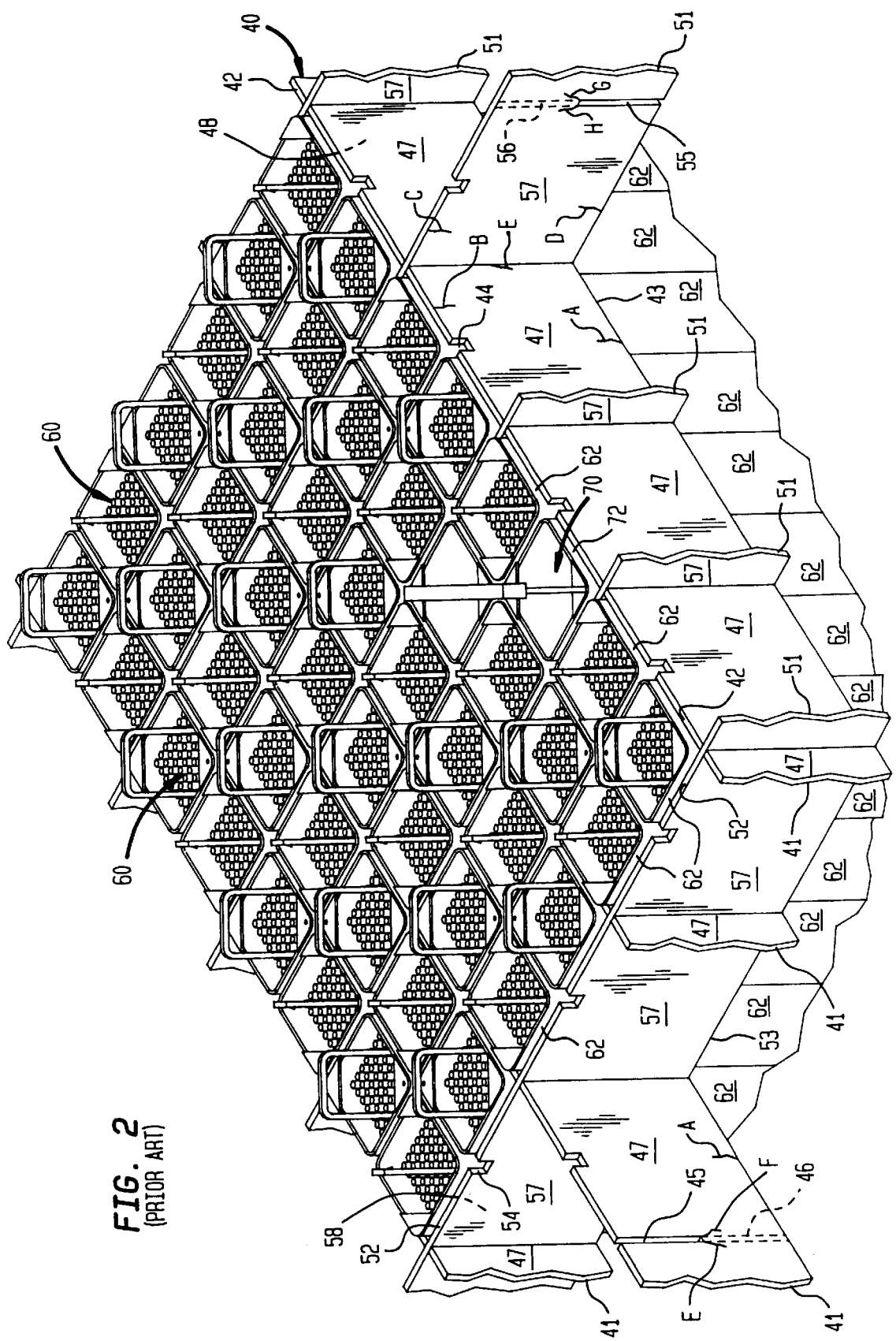
FIG. 2 is an enlarged schematic illustration of a portion of the top guide structure in FIG. 1 and showing the tops of the nuclear fuel assemblies extending into openings formed by the grid members of the top guide structure.

Referring to FIG. 1, a reactor pressure vessel 10 of a boiling water reactor is shown during shutdown and refueling operations with nuclear fuel assemblies 60 positioned underwater within the reactor core between the core support plate 20 and the top guide structure 40 and with control rods 32 which have cruciform cross-sectionally shaped blades 34 containing neutron absorbing material inserted into the gaps or spaces between fuel assemblies 60. Most of the control rods 32 have been eliminated for clarity of illustration. Referring to FIG. 2 which is an enlarged view of a portion of the top guide structure and the top portions of the nuclear fuel assemblies shown in FIG. 1, top guide structure 40 is comprised of a set of parallel grid members 41 and a second set of parallel grid members 51 which intersect to form a lattice of rectangular shaped fuel cells. The top portions of four nuclear fuel assemblies 60 and one control rod (not shown) pass through and are supported by and within each fuel cell. During refueling operations, when less than four fuel assemblies are positioned within a fuel cell in the top guide structure, a blade guide 70 is inserted in the place of the removed fuel assemblies to provide support and guidance for the control rod blades. Blade guide 70 is comprised of two dummy fuel assemblies oriented at each of their corner edges and whose handles are connected by a cross member which has a similar handle.

In accordance with the present invention, an Ultrasonic Inspection System 200 is provided for the ultrasonic inspection of the top guide structure of the reactor pressure vessel without the need for the removal of any of the fuel assemblies from the reactor core and which is mounted to a reactor pressure vessel top guide structure inspection apparatus and transport system 1. Reactor pressure vessel top guide structure inspection apparatus and transport system comprises a remotely operated and controlled powered underwater crawler vehicle 100 that rides on the top edges of two parallel grid members of the top guide structure. None of the fuel assemblies need to be removed from the reactor core for the underwater crawler vehicles to be able to traverse across and gain access to selected locations on the top of the top guide structure. Reactor pressure vessel top guide structure inspection apparatus and transport system uses the channel walls of fuel assemblies which extend above the top edges of the top guide structure as guides to ensure precise travel and positioning along the top guide structure. Reactor pressure vessel top guide structure inspection apparatus and transport system accurately maneuvers and positions Ultrasonic Inspection System 200 to selected locations on the top guide structure to enable the volumetric inspection of each grid member of the top guide structure of either a fully loaded or partially loaded reactor core. None of the fuel assemblies need to be removed from the reactor core in order for Ultrasonic Inspection System 200 to be able to volumetrically inspect the top guide structure. Similarly, if some or all of the fuel assemblies are removed from the core, whether or not the removed fuel assemblies are replaced by blade guides, the underwater crawler vehicle can traverse across the top guide structure and position Ultrasonic Inspection System 200 to inspect the top guide structure.

Figure 3:
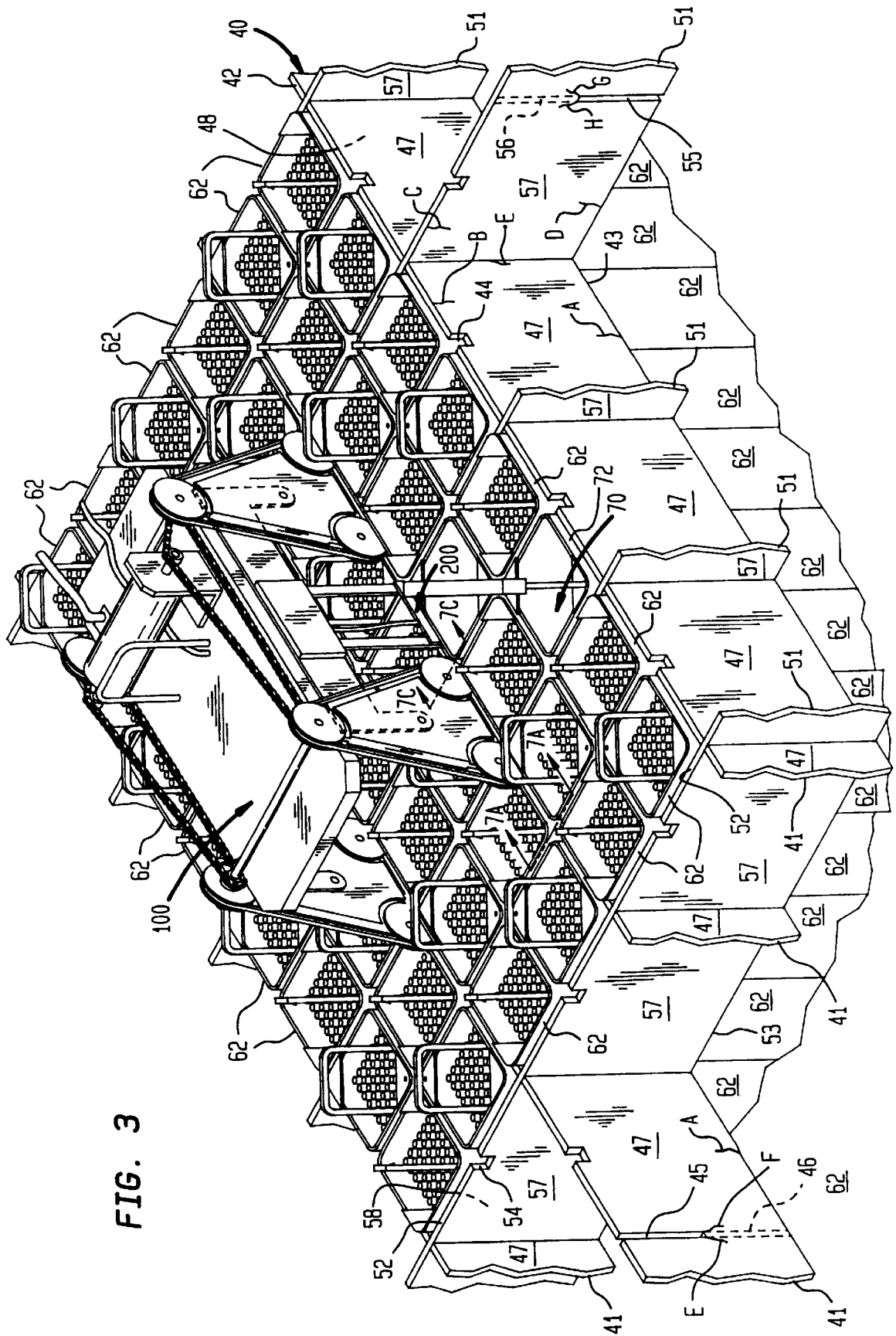
FIG. 3 is an enlarged schematic illustration of the Ultrasonic Inspection System mounted to the reactor pressure vessel top guide structure inspection apparatus and transport system which positions the Ultrasonic Inspection System on top of the top guide structure shown in FIGS. 1 and 2.

Referring to FIG. 3, underwater crawler vehicle 100 is shown with Ultrasonic Inspection System 200 mounted thereto and positioned on top guide structure 40. In accordance with the present invention, Ultrasonic Inspection System 200 can perform the inspections for irradiated assisted stress corrosion cracking and intergranular stress corrosion cracking remotely, more effectively and accurately, and without the need to remove any fuel assembly from the reactor core.

Figure 4A:
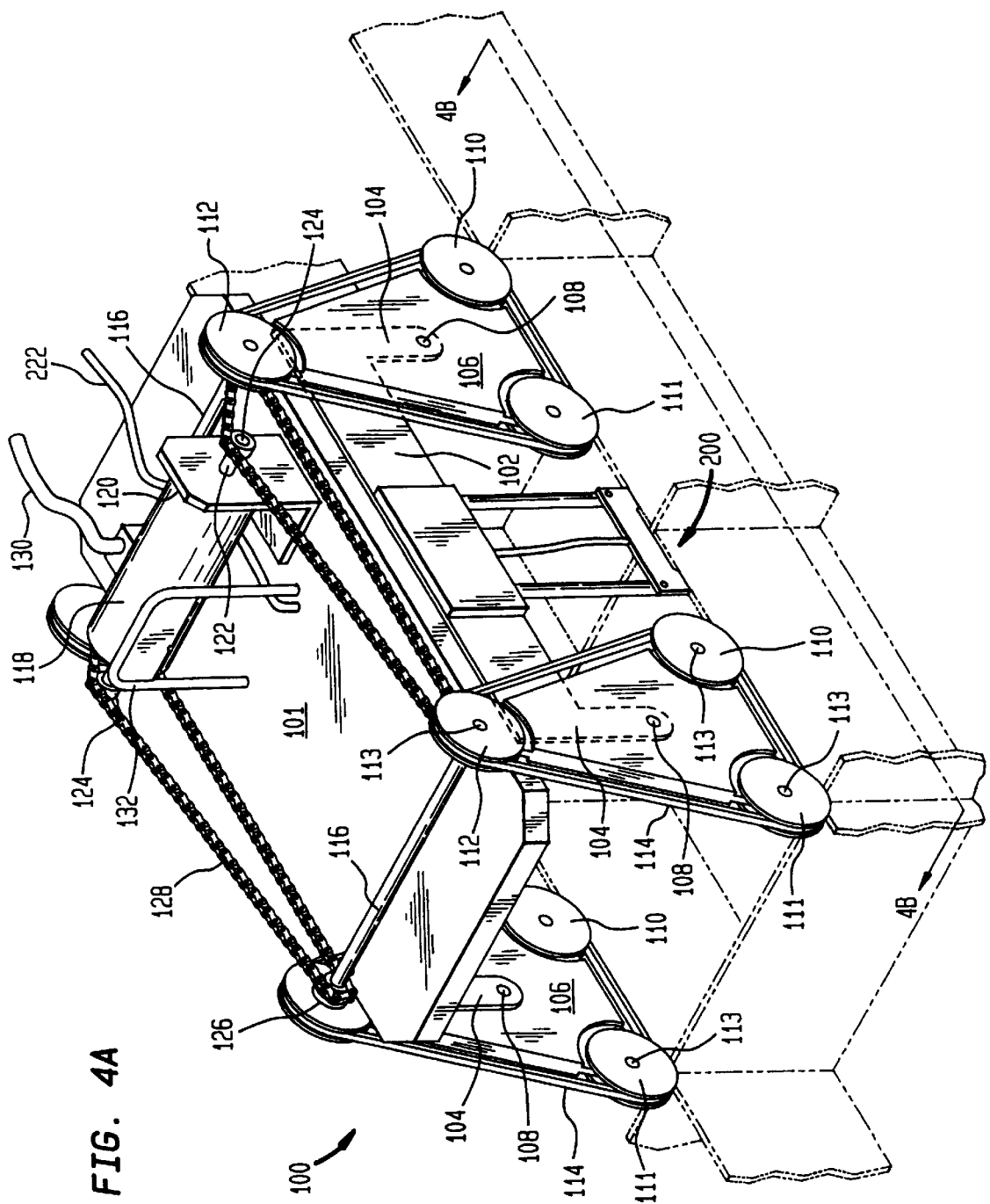
FIG. 4A is an isolated perspective view of the reactor pressure vessel top guide structure inspection apparatus and transport system shown in FIG. 3.
Figure 6:
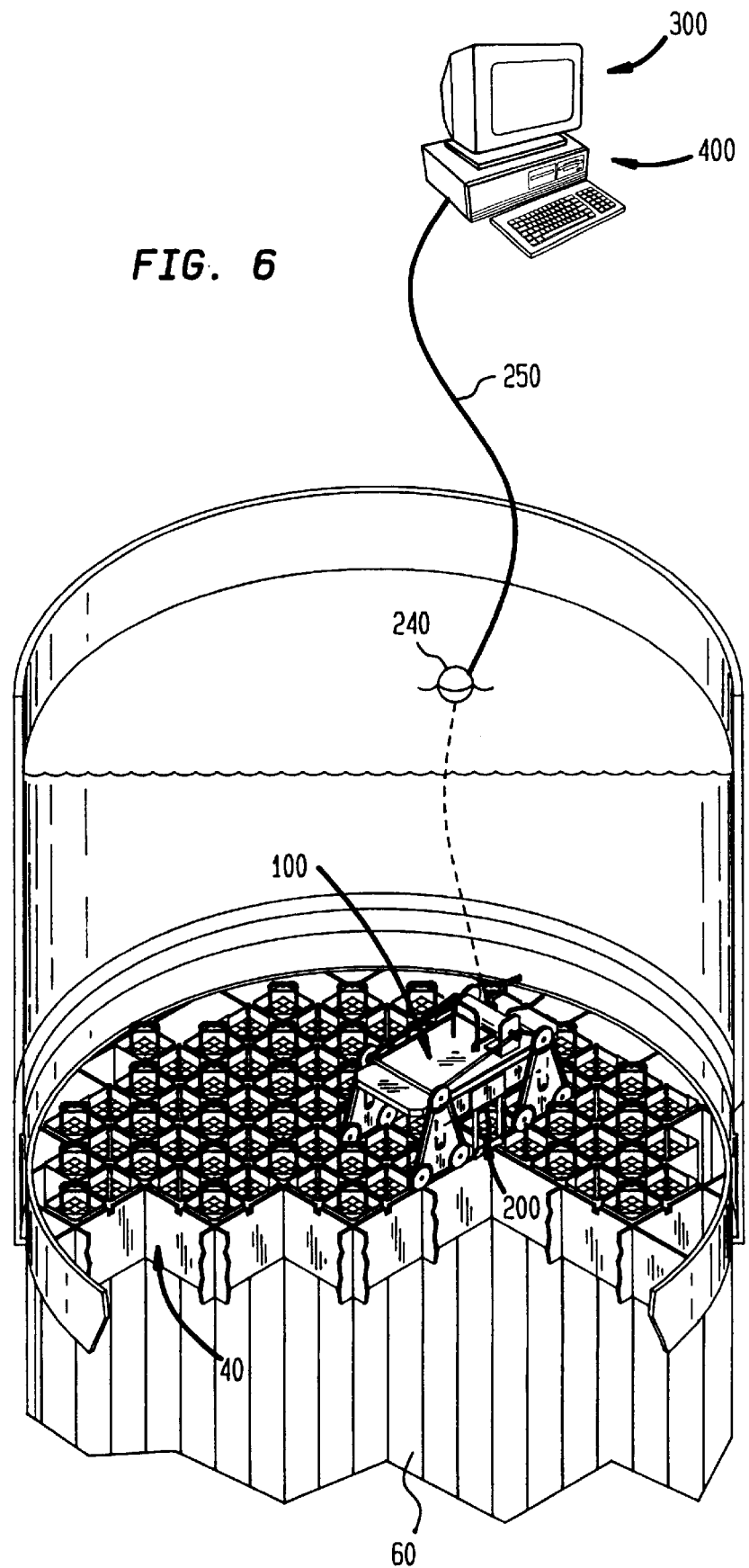
FIG. 6 is a schematic of the reactor pressure vessel top guide structure inspection apparatus and transport system shown in FIGS. 3–5 and a data acquisition unit and a control unit for collecting inspection results and for controlling the movement of the reactor pressure vessel top guide structure inspection apparatus and transport system.

Referring generally to FIGS. 3, 4A, 4B and particularly to FIG. 5, Ultrasonic Inspection System 200 comprises two integrated transducer packages one of which is located on each side of underwater crawler vehicle between each of the two bogie plates. Each package includes three integrated ultrasonic transducers, two focused angle beam or shear wave transducers (216, 218) which are positioned to face in opposite directions (216 facing forward 30° from normal to the top edge of the grid structure and 218 facing rearward 30° from normal to the top edge of the grid structure) and a creeping wave transducer 214. Defects in grid members 41 (or 51) are typically: (a) cracks extending from the top and bottom edges 42, 43 (or 52, 53) and illustrated in FIGS. 2, 3, and 5 by lines A, B, C, and D; as well as (b) cracks extending from the corners of notches 45 (or 55) and similarly illustrated in FIGS. 2, 3 and 5 by lines E, F, G, and H. Creeping wave transducer 214 generates an ultrasonic signal that penetrates and inspects the material volume of grid members 41 (or 51) close to top edge 42 (or 52) identifying defects in these surfaces. Shear wave transducers 216 and 218 each introduces an ultrasonic signal into members 41 (or 51) at a 30° angle as discussed above which has been determined to provide optimum volumetric inspection coverage. The ultrasonic signals introduced into top edges 42 (or 52) travel through the grid member and detect defects on the bottom edges 43 (or 53), as well as the notch area 45. As underwater crawler vehicle 100 is advanced, the ultrasonic signal is partially blocked from inspecting the bottom edge of the grid member by notch 45 (or 55 depending on the orientation of the crawler). Inspection coverage of this partially blocked area is provided by the rearward facing transducer 218 after the underwater crawler vehicle has advanced sufficiently past the notch providing for 100% inspection of bottom edges 43 (or 53). Additionally, the ultrasonic signals from transducers 216 and 218 are reflected from the bottom edge 43 (or 53) at the same incidence angle enabling inspection of notch area 55. Inspection of the notch areas is of particular importance since these areas are inaccessible when the fuel assemblies are in the reactor. Even if the fuel assemblies have been removed, cracks in these areas cannot normally be detected by prior art devices because such cracks are typically obscured by the notch of the complementary grid member of the top guide structure. The number, types, and positioning of the transducers ill Ultrasonic Inspection System 200 on the underwater crawler vehicle 100 enables more than 95% full volumetric inspection of the top guide structure without having to remove any fuel assembly from the core.

Each integrated transducer package includes a mounting plate 206 which is attached to flange 102 of underwater crawler system 100 by two rods 202 each of which is spring loaded 204 to maintain the transducer package in contact with and a fixed distance from the top edge of the grid member and thereby ensure sound coupling into the grid member. At the front and rear of mounting plate 206 are curved lead-in shoes 208 that prevent the transducer package from catching as it passes across possibly uneven surfaces such as the intersection of grid members 41 and 51, or alignment notches 44, 54 in the top edges of the top guide structure. Ultrasonic transducers 214, 216, 218 are mounted to a common delay line block 210 which permits installation of the transducers. Each section of delay line block 210 has an acoustic barrier 212 to ultrasonically isolate each transducer.

As shown in more detail in FIG. 4A, underwater crawler vehicle 100 comprises a central frame 101 to which two bogie plates 106 are attached two to each side. Each of the four bogie plates 106 has three wheels 110, 111, 112, arranged in a triangular array and positioned by pins 113, as well as a continuous tractor type tread or track 114 extending around the three wheels to form a tread for moving underwater crawler vehicle 100 by engaging the top edges 42, 52 of top guide structure 40. The height of bogie plate 106 is chosen so that the vehicle chassis (i.e. central frame 101) will clear the topmost portion of the fuel assemblies or blade guides (i.e. the fuel assembly handling bail and the blade guide handling bail). Projecting downward from each side edge of central frame 101 is a flange 102 having two mounting struts 104 for mounting bogie plates 106. Each bogie plate 106 has a center mounting pin 108 for mounting bogie plate 106 to bogie plate mounting strut 104 and which provides a center pivot point and permits compliance and proper alignment of the track 114 with top edges 42, 52 of the top guide structure.

The drive system comprises a reversible direct current motor 118 which provides the motive power to drive the four tracks 114 on two parallel grid members (41 or 51) causing movement along the top guide structure. Motor 118 is mounted to frame 101 by mounting flange 120 to drive shaft 122 each end of which is fitted with a motor sprocket 124. Power is transferred from motor 118 to enable the movement of underwater crawler vehicle 100 by two continuous chain drives 128 each of which is engaged and driven by motor sprocket 124. Each continuous chain drive 128 engages a sprocket 126 mounted on each end of shaft 116 connecting the top wheel 112 of each parallel bogie plate 106. When motor 118 is energized via cable 130, sprockets 124 which are rotated by motor 118 engage chains 128 and rotate sprockets 126 which in turn cause each top wheel 112 of each bogie plate 106 to rotate thereby enabling each track 114 to be driven synchronously, at variable speed, and in either a forward or a reverse direction. Motor 118 is equipped with a magnetic position encoder which transmits position information to a control console for remote operation of the underwater crawler vehicle and for correlating inspection data with the particular location of the inspection on the top grid structure.

Underwater crawler vehicle 100 is lifted by bail handle 132 by a fuel handling machine (not shown) and is placed on top edge 42 (or 52) of parallel grid members 41 (or 51). The fuel handling machine grasps the bail handle 132 of underwater crawler vehicle 100 and positions it to the starting point for the inspection, typically at the periphery of the top guide structure. Referring to FIG. 3, underwater crawler vehicle 100 is shown positioned on top edges 42 of two adjacent parallel grid members 41. Once the underwater crawler vehicle reaches the opposite end of the span of the grid members of top guide structure, the fuel handling machine is used to grasp bail handle 132 to lift underwater crawler vehicle and position it on the next span of parallel grid members. Since the underwater crawler vehicle has a reversible DC motor which propels it in either a forward or a reverse direction, the underwater crawler vehicle can be rotated 180° prior to positioning on the next span of parallel grid members, or driven in reverse on the next span. After the underwater crawler vehicle is positioned and released, the fuel handling machine is free to move fuel or perform other duties. This procedure is repeated until each span of grid members of the top guide structure is traversed.

Figure 7A:
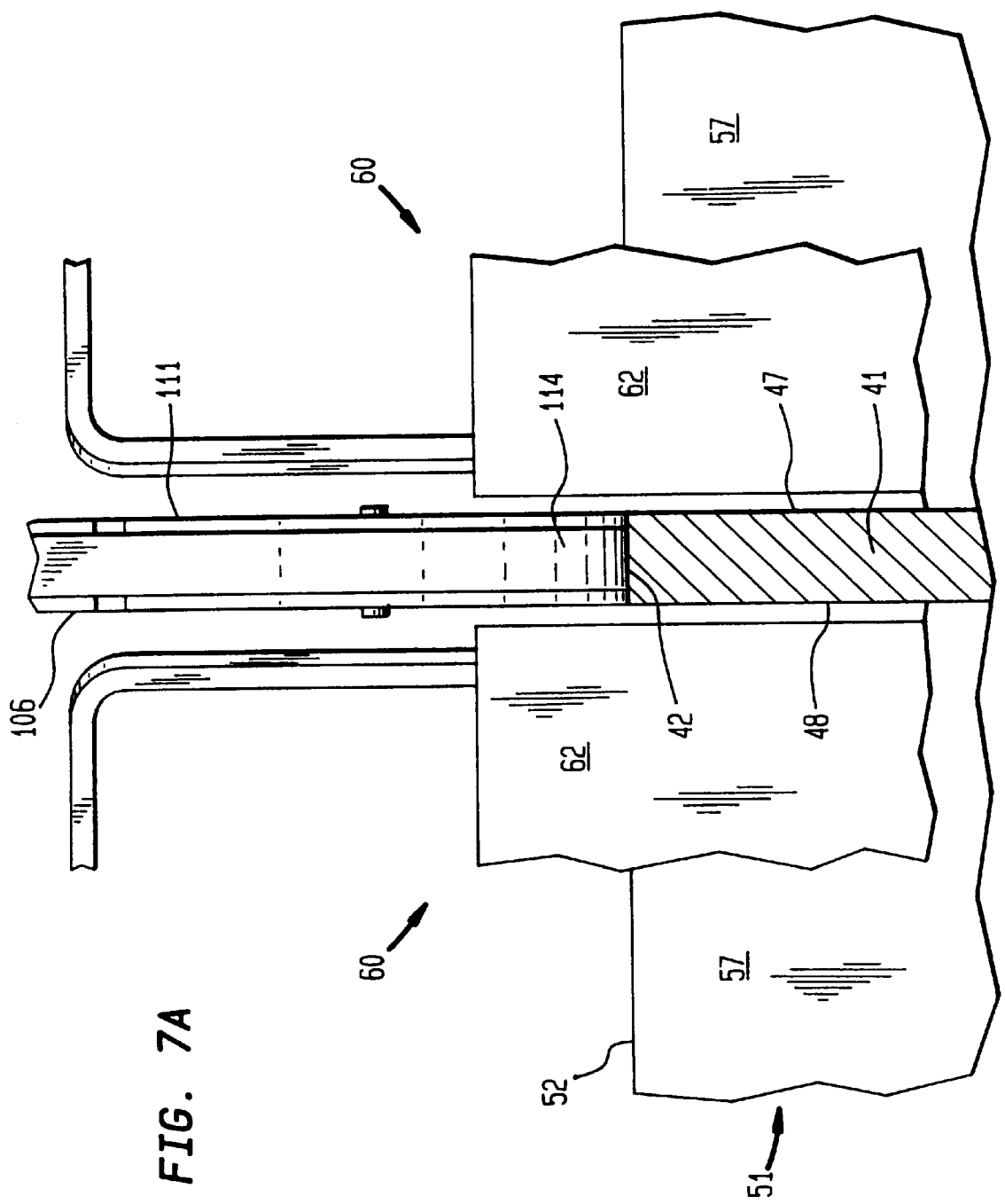
FIG. 7A is an enlarged view of one of the bottom wheels and track of the reactor pressure vessel top guide structure inspection apparatus and transport system taken along line 7A—7A in FIG. 3 as it sits upon the top grid structure and between the outer channel walls of adjacent nuclear fuel assemblies.
Figure 7B:
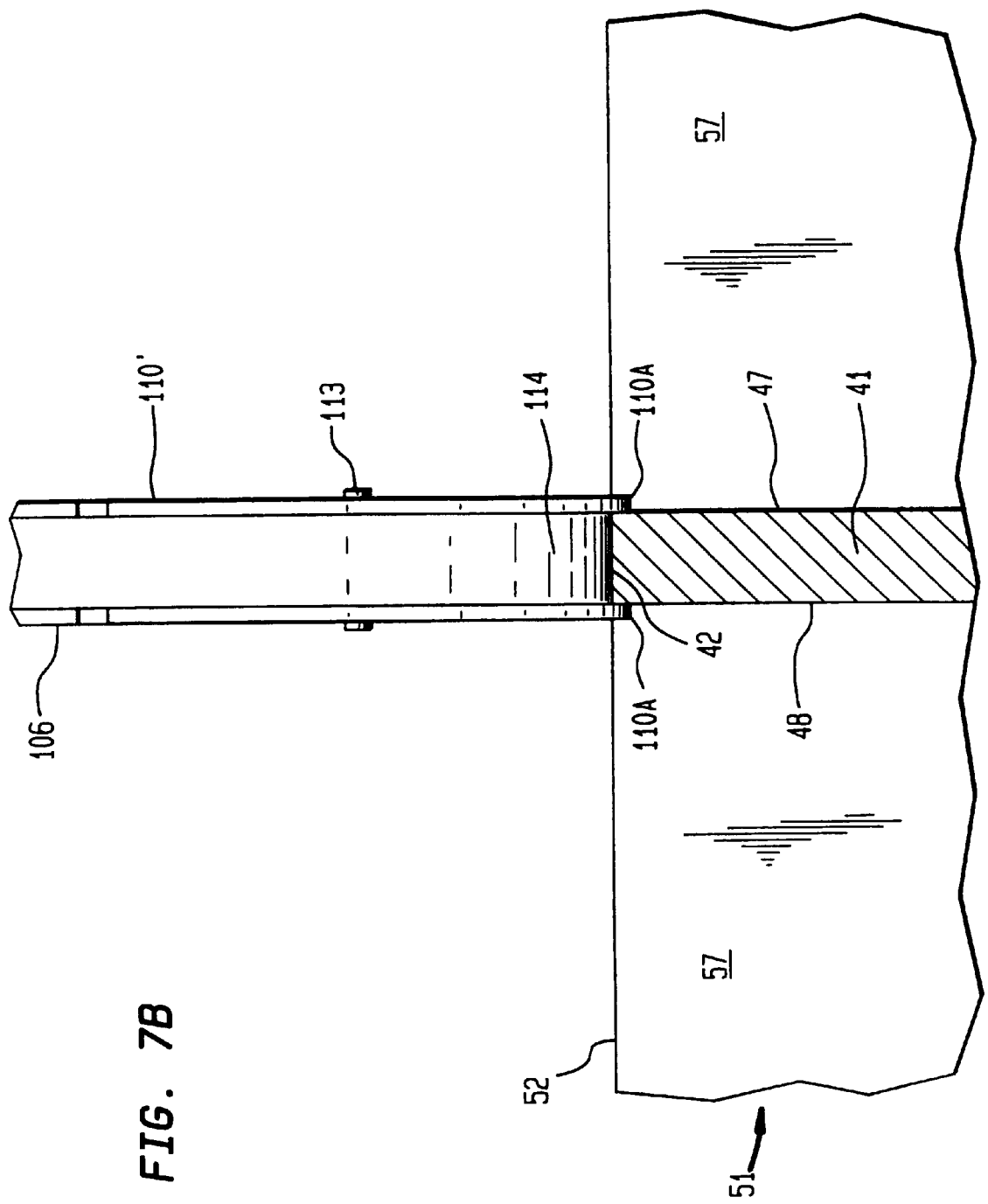
FIG. 7B is an enlarged view of one of the bottom wheels and track of an alternative embodiment as it sits upon the top grid structure with the fuel assemblies unloaded from the reactor core.
Figure 7C:
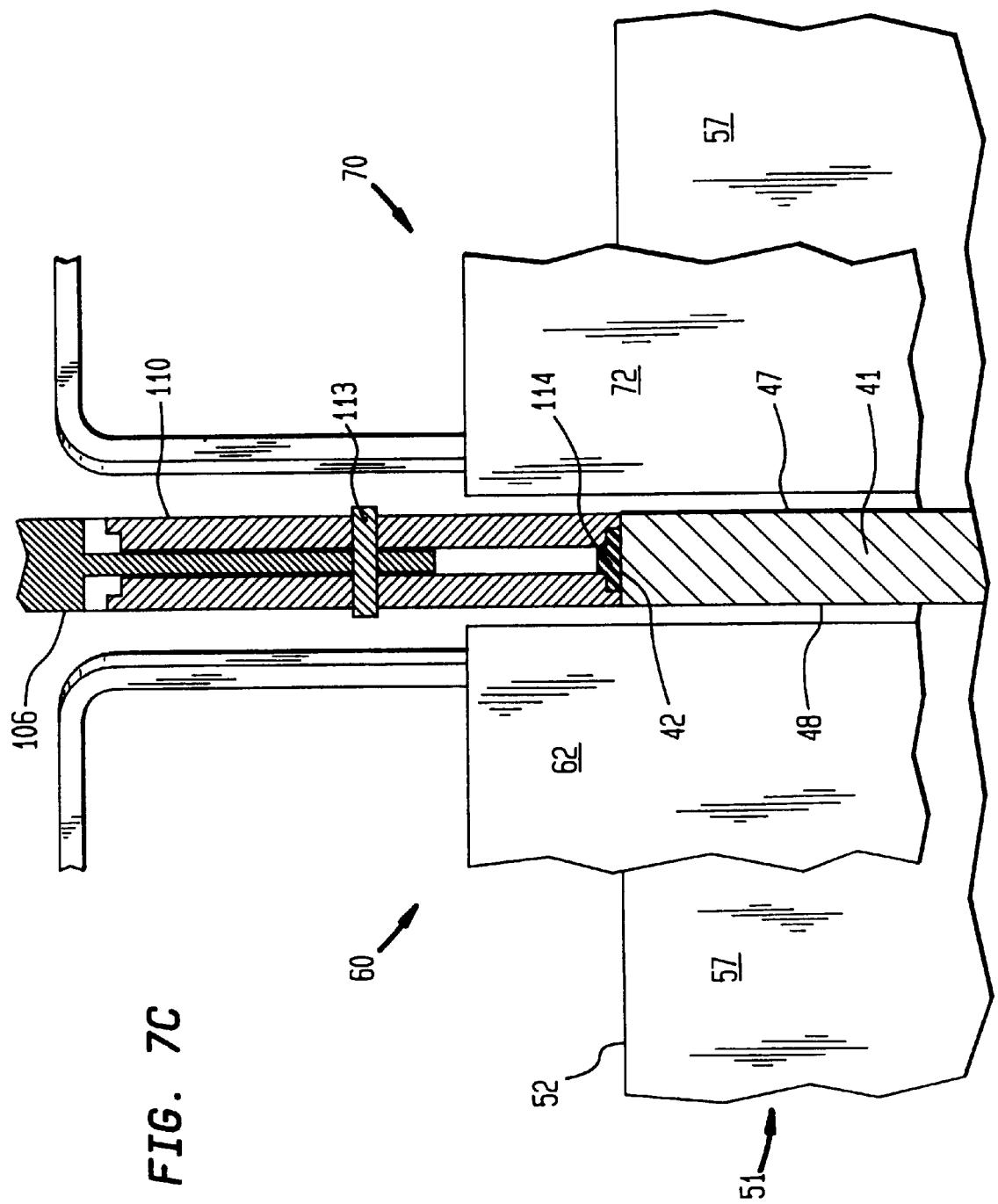
FIG. 7C is an enlarged sectional view taken along line 7C—7C in FIG. 3 of one of the bottom wheels and track as it sits upon the top grid structure and between an outer channel wall of one nuclear fuel assembly and an outer wall of an adjacent dummy fuel assembly or blade guide.

Referring to FIG. 7A which is an enlarged view, partly in section, taken along line 7A—7A in FIG. 3, track 114 on wheel 111 is shown positioned on top edge 42 of grid member 41 between channel walls 62 of adjacent fuel assemblies 60. As underwater crawler vehicle 100 is driven along the top edge 42 of the top guide structure, wheel 111 is guided by outer channel walls 62 of adjacent fuel assemblies. By having track 114 travel within a recess within each wheel, and by having the wheels ride on the top edge of the top grid structure between the channel walls 62 of adjacent fuel assemblies 60, the possibility of misalignment of track 114 from top edge 42 of the top guide structure is eliminated. In the event that blade guides 70 are inserted into the core in place of any of the fuel assemblies that may have been removed (FIG. 3), then outer walls 72 of blade guide 70 function in the same way as outer channel walls 62 of fuel assembly 60 to guide wheels 110, 111 and similarly limit any potential misalignment of track 114 relative to the top edge 42 of the top guide structure (FIG. 7C). If the nuclear fuel assemblies are removed from the core and are not replaced by blade guides, then a modified wheel 110' can be provided having extended projections 110A within which tread 114 is positioned and maintained (FIG. 7B). Unlike wheels 110, 111 projections 110A of modified wheel 110' extend below top edge 42 and engage the side surfaces 47 and 48 of grid member 41 which thereby prohibit misalignment of wheel 110' from the grid member. Thus, underwater crawler vehicle 100 can traverse across the top edges of top guide structure 40 if some, none, or all of the nuclear fuel assemblies or blade guides are removed from the core.

Control, operation, and data acquisition and storage from and to Ultrasonic Inspection System 200 and/or the underwater crawler vehicle 100 is performed from Control Console 400 utilizing a conventional computer based multichannel ultrasonic electronics system and a Data Acquisition Unit 300 which are connected via a cable bundle 250 comprised of transducer cables 222, motor cables 130 and television camera cable (not shown). Cable bundle 250 is supported by a buoyancy device 240 which floats on the surface of the water in the reactor vessel and prevents extraneous forces from moving the underwater crawler vehicle.

Referring to FIG. 8, direct current motor 118 is energized by a direct current voltage generated by DC power supply 322. The voltage level supplied to motor 118 is varied by a speed control 320, providing the underwater crawler vehicle with an infinitely variable speed range within the maximum output voltage of the power supply. Forward and reverse direction of the underwater crawler system is provided by a polarity reversing switch 318. As the underwater crawler vehicle travels along the grid members 41 (or 51) of the top guide structure, a computer 310 provides timing and control signals to a transmitter and receiver multiplexer 302 causing ultrasonic transducers 214, 216 and 218 on each side of the underwater crawler system to operate sequentially via cables 222. The return ultrasonic signal from a transducer containing inspection information is routed to a receiver 306 for initial processing. The processed signal is fed to a data analysis system 308 for further data processing and defect identification. In the data analysis system, position information from the motor position counter/scaler 316 is added to the ultrasonic data to provide physical position information of each defect. The complete data set from the transducer is then sent to computer 310 for short term storage in memory 312 or in long term disk storage 314. After computer 310 has stored the data, the clock/control/timing section of computer 310 indexes multiplexer 302 to the next transducer, and the data acquisition sequence is repeated. Computer 310 will index the multiplexer through all ultrasonic transducers in a continuous looping fashion at a rate in excess of 1 kHz.

While the present invention has been particularly shown and described with reference to preferred embodiments thereof, it will be understood by those skilled in the art that various changes in form and details may be made therein without departing from the spirit and scope of the invention.

We claim:

1. An ultrasonic inspection system for ultrasonically inspecting a top guide structure of a reactor pressure vessel of a nuclear reactor, the top guide structure comprised of two sets of parallel grid members which are interconnected to form a lattice of rectangular shaped openings, said inspection system comprising:

two shear wave transducers and a creeping wave transducer, a first one of the two shear wave transducers positioned to face in a first direction about 30° from normal to a top edge of the two sets of parallel grid members of the top guide structure and a second one of the two shear wave transducers positioned to face in a second direction about 30° from normal to the top edge of the two sets of parallel grid members of the top guide structure.

2. An ultrasonic inspection system for ultrasonic inspection of the top guide structure of a reactor pressure vessel of a nuclear reactor, the top guide structure formed by the intersection of two sets of parallel grid members having top edges and side walls, said grid members being interconnected to form a lattice of rectangular shaped openings, said ultrasonic inspection system comprising:

at least two shear wave transducers, one of the at least two shear wave transducers positioned to face in a first direction about 30° from normal to a top edge of the two sets of parallel grid members of the top guide structure and a second of the at least two shear wave transducers positioned to face in a second direction about 30° from normal to the top edge of the two sets of parallel grid members of the top guide structure.

* * * * *